United States Patent
Murakami et al.

(10) Patent No.: US 7,985,287 B2
(45) Date of Patent: *Jul. 26, 2011

(54) ANTHRAPYRIDONE COMPOUND OR A SALT THEREOF, MAGENTA INK COMPOSITION CONTAINING THE ANTHRAPYRIDONE COMPOUND AND COLORED PRODUCT

(75) Inventors: Yasuo Murakami, Tokyo (JP); Yutaka Ishii, Tokyo (JP); Noriko Kajiura, Tokyo (JP); Hiroyuki Matsumoto, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/812,711

(22) PCT Filed: Jan. 20, 2009

(86) PCT No.: PCT/JP2009/000170
§ 371 (c)(1), (2), (4) Date: Jul. 13, 2010

(87) PCT Pub. No.: WO2009/093433
PCT Pub. Date: Jul. 30, 2009

(65) Prior Publication Data
US 2010/0291360 A1    Nov. 18, 2010

(30) Foreign Application Priority Data
Jan. 25, 2008  (JP) .................... 2008-014952

(51) Int. Cl.
C09D 11/02 (2006.01)
C07D 221/18 (2006.01)
B41M 5/50 (2006.01)
B41J 2/01 (2006.01)

(52) U.S. Cl. .............. 106/31.47; 546/76; 428/195.1; 347/100

(58) Field of Classification Search .......... 106/31.47; 546/76; 428/195.1; 347/100
See application file for complete search history.

(56) References Cited

U.S. PATENT DOCUMENTS

| | | |
|---|---|---|
| 4,902,798 A | 2/1990 | Nakamatsu et al. |
| 5,367,075 A | 11/1994 | Nakamatsu et al. |
| 6,152,969 A | 11/2000 | Matsumoto et al. |
| 6,471,760 B1 | 10/2002 | Matsumoto et al. |
| 6,843,839 B2 | 1/2005 | Kanke et al. |
| 6,852,154 B2 | 2/2005 | Kitamura et al. |
| 6,929,361 B2 | 8/2005 | Matsumoto et al. |
| 6,949,135 B2 | 9/2005 | Ishibashi et al. |
| 6,984,032 B2 | 1/2006 | Kitamura et al. |
| 7,015,327 B2 | 3/2006 | Matsumoto et al. |
| 7,223,301 B2 | 5/2007 | Matsumoto et al. |
| 7,416,592 B2 | 8/2008 | Kitamura et al. |
| 7,618,484 B2 | 11/2009 | Fujimoto et al. |
| 7,678,185 B2 | 3/2010 | Matsumoto et al. |
| 7,691,191 B2 | 4/2010 | Matsumoto et al. |
| 7,785,411 B2 | 8/2010 | Ishii et al. |
| 2004/0239739 A1 | 12/2004 | Matsumoto et al. |
| 2005/0171351 A1 | 8/2005 | Matsumoto et al. |
| 2006/0219131 A1 | 10/2006 | Matsumoto et al. |

(Continued)

FOREIGN PATENT DOCUMENTS
JP    63-139170 A    6/1988
(Continued)

OTHER PUBLICATIONS

International Search Report dated Apr. 21, 2009 in corresponding foreign application (PCT/JP2009/000170).
(Continued)

*Primary Examiner* — Helene Klemanski
(74) *Attorney, Agent, or Firm* — Nields, Lemack & Frame, LLC

(57) ABSTRACT

The present invention relates to a novel anthrapyridone compound represented by the following formula (1) or a salt thereof:

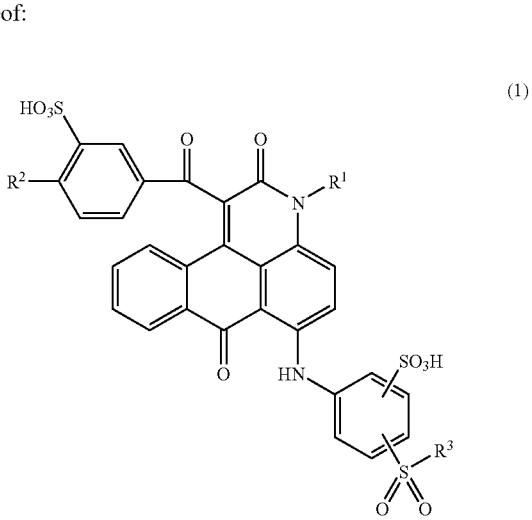

(1)

wherein, $R^1$ represents a hydrogen atom, an alkyl group or the like, $R^2$ represents a hydrogen atom or a methoxy group and $R^3$ represents an unsubstituted or substituted aryl group, or an unsubstituted or substituted a heteroaryl group, respectively; and with regard to the substitution positions of $—SO_2R^3$ and $—SO_3H$ whose substitution position are not specified and the both of which the benzene ring has thereon, one of their substitution positions is the para-position and the other thereof is the ortho-position to the substitution position of the nitrogen atom by which said benzene ring is substituted, and the compound of the present invention or a salt thereof has a hue which possesses high vividness suitable for inkjet recording, and provides a magenta coloring matter having higher fastnesses on recorded matter and excellent storage stability.

17 Claims, No Drawings

U.S. PATENT DOCUMENTS

| | | |
|---|---|---|
| 2009/0047430 A1 | 2/2009 | Mori et al. |
| 2010/0075112 A1 | 3/2010 | Ishii et al. |
| 2010/0209678 A1* | 8/2010 | Ono et al. .................. 428/195.1 |

FOREIGN PATENT DOCUMENTS

| | | |
|---|---|---|
| JP | 10-306221 A | 11/1998 |
| JP | 11-029714 A | 2/1999 |
| JP | 2000-256587 A | 9/2000 |
| JP | 2001-354881 A | 12/2001 |
| JP | 2003-335989 A | 11/2003 |
| JP | 2005-8868 A | 1/2005 |
| JP | 2005-126587 A | 5/2005 |
| JP | 2005-307067 A | 11/2005 |
| JP | 2005-307068 A | 11/2005 |
| JP | 2006-083330 A | 3/2006 |
| JP | 2007-077256 A | 3/2007 |
| JP | 2008-202011 A | 9/2008 |
| JP | 2008-280467 A | 11/2008 |
| WO | 98/11167 A1 | 3/1998 |
| WO | 03/027185 A1 | 4/2003 |
| WO | 2008/056699 A1 | 5/2008 |

OTHER PUBLICATIONS

International Search Report dated Jan. 29, 2008 cited in US7785411 (PCT/JP2007/071631).

International Search Report dated Jan. 8, 2008 cited in US7691191 (PCT/JP2007/072821).

International Search Report dated Jan. 8, 2008 cited in US7678185 (PCT/JP2007/072909).

* cited by examiner

ANTHRAPYRIDONE COMPOUND OR A SALT THEREOF, MAGENTA INK COMPOSITION CONTAINING THE ANTHRAPYRIDONE COMPOUND AND COLORED PRODUCT

TECHNICAL FIELD

The present invention relates to a novel anthrapyridone compound, a magenta ink composition containing the anthrapyridone compound as a coloring matter and a colored product colored with these.

BACKGROUND ART

In the recording method by means of an inkjet printer which is one of the typical methods among various color recording methods, various methods for discharging ink have been developed. In any of the methods, ink droplets are generated and adhered onto various record-receiving materials (such as paper, film and cloth) to perform recording. This has been rapidly prevailing lately and is expected to continue growing remarkably in the future because of features such as quietness with almost no noise generation due to no direct contact of a recording head with a record-receiving material and as easiness in downsizing, speeding-up and colorization.

Conventionally, as ink for fountain pens, felt-tip pens or the like and as ink for inkjet recording, water-based inks where a water-soluble dye is dissolved an aqueous medium have been used. In these water-based inks, a water-soluble organic solvent is generally added to prevent ink from clogging at a pen tip or an inkjet nozzle. These conventional inks are required to provide recorded images with sufficient density, not to clog at a pen tip or a nozzle, to dry quickly on a record-receiving material, to bleed less, to have excellent storage stability, and so on. In addition, recorded images formed are required to have fastnesses such as water fastness, light fastness and moisture fastness.

Meanwhile, images or character information on color displays of computers are generally expressed by subtractive color mixing of 4 color inks of yellow (Y), magenta (M), cyan (C) and black (K) for color recording by an ink jet printer. In order that the hue of an image expressed by additive color mixing of red (R), green (G) and blue (B) on CRT displays and the like is, as faithfully as possible, reproduced with an image expressed by subtractive color mixing, it is desired that each of Y, M and C has a hue as close to each standard as possible and also is vivid. In addition, it is required that ink compositions to be used for them are stable in storage for a long period of time, and that images printed therewith have a high concentration and said images are excellent in fastnesses such as water fastness, light fastness, and gas fastness.

The application of inkjet printers has been widely spread in the fields ranging from small printers for office automation to large printers for industrial use, and therefore fastnesses such as water fastness, moisture fastness, light fastness and gas fastness have been required more than ever. Water fastness has been largely improved by coating organic or inorganic particulates of porous silica, cation polymer, aluminasol, special ceramic and the like together with a PVA resin on a paper surface to provide an image receiving layer on a record-receiving material, and otherwise. Moisture fastness means durability against the phenomenon that a dye in a record-receiving material bleeds around a colored image when the colored record-receiving material is stored under an atmosphere of high humidity (also referred to as bleeding). Dye bleeding extremely deteriorates image quality in images particularly required to have a high resolution and photo-like image quality, and therefore it is important to reduce such bleeding as far as possible. As for light fastness, the technique for large improvement thereof has not established yet. In particular, many of coloring matters for magenta among 4 primary colors of Y, M, C and K originally have low light fastness, and therefore improvement thereof is an important problem. In addition, there are more opportunities to print pictures at home with recent spread of digital cameras, and image discoloration by oxidizing gases such as ozone gas and nitrogen oxides in the air where printed matters obtained are stored is acknowledged as a problem. Oxidizing gas has a nature to react with dyes on or in a recorded paper, causing discoloration or fading of the printed image. Among oxidizing gasses, ozone gas is regarded as a main causative matter accelerating color-fading phenomenon of inkjet-recorded images. This phenomenon of discoloration or fading is characteristic of inkjet images, and therefore improvement of ozone gas fastness is an important problem as well as improvement of light fastness.

As a magenta coloring matter used in water-soluble inks for inkjet recording, typical are xanthene-based coloring matters and azo-based coloring matters using H acid (1-amino-8-hydroxy-naphthalene-3,6-disulfonic acid). However, the former is very excellent in hue and vividness but very inferior in light fastness. On the other hand, in the latter, some are good in terms of hue and water fastness, but many are inferior in light fastness and vividness. As the latter type, a magenta dye having improved vividness and light fastness has been developed but it still has a low level in light fastness compared with dyes having a different hue such as a cyan dye represented by a copper phthalocyanine-based coloring matter and a yellow dye.

A coloring matter for magenta excellent in vividness and light fastness includes an anthrapyridone-based coloring matter (see, for example, Patent Literatures 1 to 11), but a coloring matter for magenta satisfying all the requirements on hue, vividness, light fastness, water fastness, gas fastness and dissolving stability has yet to be obtained.

[Patent Literature 1] JP 10-306221 A (pp. 1-3 and pp. 7-18)
[Patent Literature 2] JP 2000-109464 A (pp. 1-2 and pp. 8-12)
[Patent Literature 3] JP 2000-169776 A (pp. 1-2 and pp. 6-9)
[Patent Literature 4] JP 2000-191660 A (pp. 1-3 and pp. 11-14)
[Patent Literature 5] JP 2000-256587 A (pp. 1-3 and pp. 7-18)
[Patent Literature 6] JP 2001-72884 A (pp. 1-2 and 8-11)
[Patent Literature 7] JP 2001-139836 A (pp. 1-2 and pp. 7-12)
[Patent Literature 8] WO 2004/104108 (pp. 20-36)
[Patent Literature 9] JP 2003-192930 A (pp. 1-4 and pp. 15-18)
[Patent Literature 10] JP 2005-8868 A (pp. 1-3 and pp. 15-22)
[Patent Literature 11] JP 2005-314514 A (pp. 1-3 and pp. 15-20)

DISCLOSURE OF THE INVENTION

Problems to Be Solved by the Invention

It is an object of the present invention to provide a magenta coloring matter (compound) having high solubility in water, a hue and vividness suitable for inkjet recording and high brightness and allowing recorded matter excellent in various fastnesses, particularly in moisture fastness and gas fastness, and an ink composition containing thereof.

Means of Solving the Problems

The present inventors have intensively studied to solve the above problems and found that an anthrapyridone compound represented by a specific formula (1), and thus the present invention has been completed. That is, the present invention relates to:

(1)
An anthrapyridone compound represented by the following formula (1) or a salt thereof:

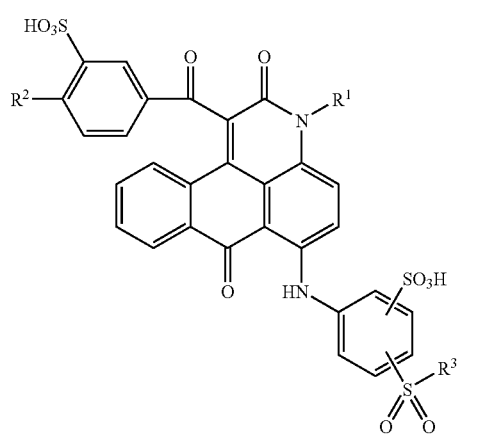

[wherein,
$R^1$ represents a hydrogen atom, a lower alkyl group, a hydroxy lower alkyl group, a cyclohexyl group, a mono- or di-lower alkylamino lower alkyl group or a cyano lower alkyl group,
$R^2$ represents a hydrogen atom or a methoxy group,
$R^3$ represents an unsubstituted C5-C12 alkyl group; a substituted C5-C12 alkyl group having, as a substituent, a group selected from the group consisting of an aryl group, a heterocyclic group, a sulfonic acid group, a carboxy group, an alkoxycarbonyl group, an acyl group, a carbamoyl group, a cyano group, an alkoxy group, a phenylalkoxy group, a phenoxy group, a hydroxy group and a nitro group; an unsubstituted aryl group; a substituted aryl group having, as a substituent, a group selected from the group consisting of a halogen atom, a cyano group, a hydroxy group, a sulfonic acid group, a substituted or unsubstituted alkyl group, a carboxy group, an alkoxycarbonyl group, a carbamoyl group, an alkoxy group, a phenoxy group and a nitro group; an unsubstituted heteroaryl group; or a substituted heteroaryl group having, as a substituent, a group selected from the group consisting of a halogen atom, a cyano group, a hydroxy group, a sulfonic acid group, a substituted or unsubstituted alkyl group, a carboxy group, an alkoxycarbonyl group, a carbamoyl group, an alkoxy group, a phenoxy group and a nitro group; respectively, and with regard to the substitution positions of —$SO_2R^3$ and —$SO_3H$ whose substitution position are not specified and the both of which the benzene ring has thereon, one of their substitution positions is the para-position and the other thereof is the ortho-position to the substitution position of the nitrogen atom by which said benzene ring is substituted], (2)
The anthrapyridone compound or a salt thereof according to the above (1), wherein:
$R^1$ is a hydrogen atom or a methyl group, (3)
The anthrapyridone compound or a salt thereof according to the above (1), wherein:
$R^1$ is a hydrogen atom or a methyl group, and
$R^3$ is an unsubstituted C6-C8 alkyl group; a substituted C6-C8 alkyl group having, as a substituent, a group selected from the group consisting of an aryl group, a heterocyclic group, a sulfonic acid group, a carboxy group, an alkoxycarbonyl group, an acyl group, a carbamoyl group, a cyano group, an alkoxy group, a phenoxy group, a hydroxy group and a nitro group; or a substituted phenyl group having, as a substituent, a sulfonic acid group or a carboxy group, (4)
The anthrapyridone compound or a salt thereof according to the above (1), wherein:
$R^1$ is a methyl group, and
$R^3$ is an unsubstituted C6 alkyl group; or a substituted phenyl group having a carboxy group as a substituent, (5)
The anthrapyridone compound or a salt thereof according to the above (4), wherein $R^2$ is a hydrogen atom, (6)
An ink composition characterized by containing, as a coloring matter, the anthrapyridone compound or a salt thereof according to any one of the above (1) to (5), (7)
The ink composition according to the above (6), which further contains water and a water-soluble organic solvent, (8)
The ink composition according to the above (7), which is for inkjet recording, (9)
The ink composition according to any one of the above (6) to (8), wherein the content of inorganic impurity contained in the total mass of the anthrapyridone compound or a salt thereof according to any one of the above (1) to (5) contained as a coloring matter is 1% by mass or less,

(10)
The ink composition according to any one of the above (6) to (9), wherein the content of the anthrapyridone compound or a salt thereof according to any one of the above (1) to (5) contained as a coloring matter is 0.1 to 20% by mass to the total mass of the ink composition,

(11)
A method for inkjet recording characterized in that recording is performed on a record-receiving material by discharging a droplet of an ink composition containing the anthrapyridone compound or a salt thereof according to any one of the above (1) to (5) or the ink composition according to any one of the above (6) to (10) responding to a recording signal,

(12)
The method for inkjet recording according to the above (11), wherein the record-receiving material is a communication sheet,

(13)
The method for inkjet recording according to the above (12), wherein the communication sheet is a communication sheet having an ink image-receiving layer containing a porous white inorganic substance,

(14)
A colored product colored with the ink composition according to any one of the above (6) to (10),

(15)
The colored product according to the above (14), wherein coloring is performed by an inkjet printer,

(16)
An inkjet printer comprising a container containing the ink composition according to any one of the above (6) to (10),

(17) The anthrapyridone compound or a salt thereof according to the above (1) or (2), wherein $R^1$ is a methyl group, and $R^3$ is an unsubstituted C6-C8 alkyl group or a carboxy-substituted aryl group.

Effect of the Invention

The anthrapyridone compound of the above formula (1) of the present invention has characteristics of exhibiting a very highly vivid and bright hue on inkjet recording paper, being excellent in water-solubility and having good filtration properties to a membrane filter in the production process of an ink composition. In addition, the ink composition of the present invention using this compound is free from crystal precipitation, changes in physical properties and color, and the like after storage for a long period of time, and thus it has good storage stability. Further, a printed matter using the anthrapyridone compound of the present invention as a magenta ink for inkjet recording has an ideal magenta hue without selecting a record-receiving material (paper, film and the like). Furthermore, the magenta ink composition of the present invention also enables the hue of a photo-like color image to be faithfully reproduced on paper. Moreover, even when recording is performed on a record-receiving material whose surface is coated with inorganic particles, such as inkjet special paper or film for photo image quality, the anthrapyridone compound of the present invention is extremely excellent in various good fastnesses, particularly in ozone gas fastness and moisture fastness and provides the photo-like recorded image with an excellent long-term storage stability. Therefore, the anthrapyridone compound of the above formula (1) is extremely useful as a coloring matter for ink for inkjet recording.

BEST MODE FOR CARRYING OUT THE INVENTION

The present invention will be specifically explained. In the present description, "anthrapyridone compound or a salt thereof of the present invention" is hereinafter referred to as simply "anthrapyridone compound of the present invention" for abbreviation due to avoid complication, unless otherwise noted.

In the present description, the "alkyl group" described here can include C1-C12 alkyl groups, and said alkyl group includes, for example, straight-chain C1-C12 alkyl groups such as methyl, ethyl, n-propyl, n-butyl, n-pentyl, n-hexyl, n-heptyl, n-octyl, n-nonyl, n-decyl, n-undecyl and n-dodecyl; branched C1-C12 alkyl groups such as iso-propyl, sec-butyl, t-butyl, iso-butyl, 2-methylbutyl, i-octyl, tert-octyl, 2-ethylhexyl and tert-nonyl; cyclic alkyl groups such as cyclopropyl, cyclobutyl, cyclopentyl and cyclohexyl; and the like. In addition, the lower alkyl group can include usually alkyl having C1-C4 carbon atoms and preferably alkyl having C1-C3 carbon atoms among the above alkyl groups. Specific examples thereof include groups included in C1-C4 alkyl and preferably groups included in C1-C3 alkyl, among the above specific examples of the alkyl group.

In the present description, in groups other than the alkyl group, for example, in alkoxy group and the like, the alkyl moiety which said alkoxy group and the like has is one of the same groups as described above for the alkyl group (with regard to the type, the range of the number of carbon atoms, and the like). Therefore, the lower alkyl moiety of lower alkoxy groups may be also, unless otherwise specifically noted, any of straight-chain, branched-chain and cyclic, and the number of carbon atoms is usually C1-C4 and preferably C1-C3.

In the description of the substituents in the present description, a group usually means an unsubstituted group if not otherwise specified that it may have a substituent.

In the present description, RTM in superscription stands for registered trademark.

The anthrapyridone compound of the present invention is represented by the above formula (1).

In the formula (1), $R^1$ represents a hydrogen atom, a lower alkyl group, a hydroxy lower alkyl group, a cyclohexyl group, a mono- or di-lower alkylamino lower alkyl group or a cyano lower alkyl group.

In the case where $R^1$ in the above formula (1) is a lower alkyl group, said lower alkyl group can include the groups described above as the lower alkyl group, including preferable ones. Specific examples thereof include preferably methyl, ethyl, n-propyl and iso-propyl and more preferably methyl.

In the case where $R^1$ is a hydroxy lower alkyl group, said lower alkyl moiety can include the groups described above as the lower alkyl group, including preferable ones. Specific examples of said hydroxy lower alkyl group include, for example, hydroxyethyl, hydroxypropyl, hydroxybutyl and the like.

Any of the lower alkyl moieties in mono-lower alkylamino lower alkyl groups for $R^1$ can include the groups described above as the lower alkyl group, including preferable ones. Specific examples of said mono-lower alkylamino lower alkyl group include, for example, methylaminopropyl, ethylaminopropyl and the like.

Any of the lower alkyl moieties in di-lower alkylamino lower alkyl groups for $R^1$ can include the groups described above as the lower alkyl group, including preferable ones. Specific examples of said di-lower alkylamino lower alkyl group, for example, dimethylaminopropyl, diethylaminoethyl and the like.

In the case where $R^1$ is a cyano lower alkyl group, said lower alkyl moiety can include the groups described above as the lower alkyl group, including preferable ones. Specific examples of said cyano lower alkyl group include, for example, cyanoethyl, cyanopropyl, cyanobutyl and the like.

$R^1$ preferably includes a hydrogen atom or a lower alkyl group, more preferably a hydrogen atom or methyl, and particularly preferably methyl.

In the above formula (1), $R^2$ represents a hydrogen atom or methoxy. These are all preferable.

In the above formula (1), $R^3$ represents an unsubstituted C5-C12 alkyl group; a substituted C5-C12 alkyl group having, as a substituent, a group selected from the group consisting of an aryl group, a heterocyclic group, a sulfonic acid group, a carboxy group, an alkoxycarbonyl group, an acyl group, a carbamoyl group, a cyano group, an alkoxy group, a phenylalkoxy group, a phenoxy group, a hydroxy group and a nitro group; an unsubstituted aryl group; a substituted aryl group having, as a substituent, a group selected from the group consisting of a halogen atom, a cyano group, a hydroxy group, a sulfonic acid group, a substituted or unsubstituted alkyl group, a carboxy group, an alkoxycarbonyl group, a carbamoyl group, an alkoxy group, a phenoxy group and a nitro group; an unsubstituted heteroaryl group; or a substituted heteroaryl group having, as a substituent, a group selected from the group consisting of a halogen atom, a cyano group, a hydroxy group, a sulfonic acid group, a substituted or unsubstituted alkyl group, a carboxy group, an alkoxycarbonyl group, a carbamoyl group, an alkoxy group, a phenoxy group and a nitro group; respectively.

In the case where $R^3$ is an unsubstituted alkyl group, said alkyl group is usually C5-C12 alkyl, preferably C5-C8 alkyl, more preferably C6-C8 alkyl and further preferably C6 alkyl. Specific examples thereof include groups having the number of carbon atoms in the range of the numbers of carbon atoms of the above unsubstituted alkyl groups among the above specific examples of the alkyl group, including the specific examples of preferable ones. These are preferably any of straight-chain, branched-chain and cyclic, but C6 ones are particularly preferably of straight-chain.

Hereinafter, the case where $R^3$ is a substituted C5-C12 alkyl group will be explained. In this case, said alkyl moiety is usually C5-C12 alkyl, preferably C5-C10 alkyl and more preferably C5-C8 alkyl. It is further preferably C5-C6 alkyl, and in some cases, it is further preferably C6-C8 alkyl and particularly preferably C6 alkyl. Specific examples of the alkyl moiety in said substituted C5-C12 alkyl group include ones having the number of carbon atoms within the range of the numbers of carbon atoms of the alkyl groups having the above substituent among the specific examples explained for the above alkyl group, including the specific examples of preferable ones. Said substituted C5-C12 alkyl group is one where any hydrogen atom of the alkyl moiety of these is replaced by a corresponding substituent.

In the case where $R^3$ is a C5-C12 alkyl group having an aryl group, said aryl group includes aryl groups consisting of C6-C14, such as phenyl, naphthyl or anthracenyl, and preferably phenyl or naphthyl. Specific examples thereof include phenyl-substituted ones, such as 5-phenylpentyl, 6-phenylhexyl, 8-phenyloctyl, 10-phenyldecyl and 12-phenyldodecyl; naphthyl-substituted ones such as 5-naphthylpentyl, 6-naphthylhexyl, 8-naphthyloctyl, 10-naphthyldecyl and 12-naphthyldodecyl; and the like.

In the case where $R^3$ is a C5-C12 alkyl group having a heterocyclic group, said hetero ring usually includes 6-membered heteroaromatic rings, preferably nitrogen-containing 6-membered heteroaromatic rings and more preferably pyridine rings. The substitution position on the pyridine ring by which the alkyl group is substituted is preferably any of the 2-, 3- and 4-positions. Specific examples of the C5-C12 alkyl group having a heterocyclic group include pyridylpentyl, pyridylhexyl, pyridyldecyl, pyridyldodecyl and the like.

In the case where $R^3$ is a C5-C12 alkyl group having a sulfonic acid group, specific examples thereof include 5-sulfopentyl, 6-sulfohexyl, 8-sulfooctyl, 10-sulfodecyl, 12-sulfododecyl and the like. Among them, preferable is 5-sulfopentyl, 6-sulfohexyl or 8-sulfooctyl and more preferable is 5-sulfopentyl or 6-sulfohexyl.

In the case where $R^3$ is a C5-C12 alkyl group having a carboxy group, specific examples thereof include carboxypentyl, carboxyhexyl, carboxyoctyl, carboxydecyl, carboxydodecyl and the like. Among them, preferable is carboxypentyl, carboxyhexyl or carboxyoctyl and more preferable is carboxypentyl or carboxyhexyl.

In the case where $R^3$ is a C5-C12 alkyl group having an alkoxycarbonyl group, a lower alkoxycarbonyl C5-C12 alkyl group is preferable. Specific examples thereof include 2-methoxycarbonylpentyl, 2-ethoxycarbonylpentyl, 2-butoxycarbonylpentyl, 3-methoxycarbonylpentyl, 4-methoxycarbonylpentyl, 5-methoxycarbonylpentyl, 6-methoxycarbonylhexyl, 8-methoxycarbonyloctyl, methoxycarbonyldecyl, methoxycarbonyldodecyl and the like. Among them, preferable are 2-methoxycarbonylpentyl, 2-ethoxycarbonylpentyl, 2-butoxycarbonylpentyl, 3-methoxycarbonylpentyl, 4-methoxycarbonylpentyl, 5-methoxycarbonylpentyl and 6-methoxycarbonylhexyl and more preferable are 5-methoxycarbonylpentyl and 6-methoxycarbonylhexyl.

In the case where $R^3$ is a C5-C12 alkyl group having an acyl group, said acyl group is preferably a lower alkylcarbonyl group, a phenyl lower alkylcarbonyl group or a phenylcarbonyl group (benzoyl group). Specific examples of the C5-C12 alkyl group having an acyl group include lower alkylcarbonyl C5-C12 alkyl groups such as 5-methylcarbonylpentyl, 6-methylcarbonylhexyl, 8-methylcarbonyloctyl, 10-methylcarbonyldecyl, 11-methylcarbonylundecyl and 12-methylcarbonyldodecyl; phenyl lower alkylcarbonyl C5-C12 alkyl groups such as 5-(2-phenylethylcarbonyl)pentyl, 6-(2-phenylethylcarbonyl)hexyl and 6-(4-phenylbutyl carbonyl)hexyl; benzoyl C5-C12 alkyl groups; or the like. Among them, preferable are 5-methylcarbonylpentyl, 6-methylcarbonylhexyl, 8-methylcarbonyloctyl, benzoyl C5-C12 alkyl groups and the like.

In the case where $R^3$ is a C5-C12 alkyl group having a carbamoyl group, specific examples thereof include 5-carbamoylpentyl, 6-carbamoylhexyl, 8-carbamoyloctyl, 10-carbamoyldecyl, 12-carbamoyldodecyl or the like. Among them, preferable is 5-carbamoylpentyl or 6-carbamoylhexyl.

In the case where $R^3$ is a C5-C12 alkyl group having a cyano group, specific examples thereof include 5-cyanopentyl, 6-cyanohexyl, 8-cyanooctyl, 10-cyanodecyl, 11-cyanoundecyl, 12-cyanododecyl or the like, and among them, preferable is 5-cyanopentyl or 6-cyanohexyl.

In the case where $R^3$ is a C5-C12 alkyl group having an alkoxy group, a lower alkoxy C5-C12 alkyl group is preferable. Specific examples thereof include 5-methoxypentyl, 5-ethoxypentyl, 5-propoxypentyl, 5-isopropoxypentyl, 5-butoxypentyl, 6-methoxyhexyl, 2-methoxyhexyl, 6-ethoxyhexyl, 6-butoxyhexyl, 8-methoxyoctyl, 10-methoxydecyl, 11-methoxyundecyl, 12-methoxydodecyl or the like. Among them, preferable is 5-methoxypentyl, 5-ethoxypentyl, 6-methoxyhexyl, 2-methoxyhexyl or 6-ethoxyhexyl and more preferable is 6-methoxyhexyl or 6-ethoxyhexyl.

In the case where $R^3$ is a C5-C12 alkyl group having a phenylalkoxy group, a phenyl lower alkoxy C5-C12 alkyl group is preferable. Specific examples thereof include 5-benzyloxypentyl, 6-benzyloxyhexyl, 8-benzyloxyoctyl, 10-benzyloxydecyl, 11-benzyloxyundecyl, 12-benzyloxydodecyl, 5-phenethyloxypentyl, 5-phenylbutoxypentyl, 6-phenethyloxyhexyl, 6-phenylbutoxyhexyl or the like. Among them, preferable is 5-benzyloxypentyl, 6-benzyloxyhexyl, 5-phenethyloxypentyl, 5-phenylbutoxypentyl, 6-phenethyloxyhexyl or 6-phenylbutoxyhexyl and more preferable is 6-phenethyloxyhexyl or 6-benzyloxyhexyl.

In the case where $R^3$ is a C5-C12 alkyl group having a phenoxy group, specific examples thereof include 5-phenoxypentyl, 6-phenoxyhexyl, 8-phenoxyoctyl, 10-phenoxydecyl, 11-phenoxyundecyl, 12-phenoxydodecyl or the like. Among them, preferable is 5-phenoxypentyl, 6-phenoxyhexyl or 8-phenoxyoctyl and more preferable is 5-phenoxypentyl or 6-phenoxyhexyl.

In the case where $R^3$ is a C5-C12 alkyl group having a hydroxy group, specific examples thereof include 5-hydroxypentyl, 6-hydroxyhexyl, 8-hydroxyoctyl, 10-hydroxydecyl, 11-hydroxyundecyl, 12-hydroxydodecyl or the like. Among them, preferable is 5-hydroxypentyl, 6-hydroxyhexyl or 8-hydroxyoctyl and more preferable is 5-hydroxypentyl or 6-hydroxyhexyl.

In the case where $R^3$ is a C5-C12 alkyl group having a nitro group, specific examples thereof include 5-nitropentyl, 6-nitrohexyl, 8-nitrooctyl, 10-nitrodecyl, 11-nitroundecyl, 12-nitrododecyl or the like. Among them, preferably it includes 5-nitropentyl, 6-nitrohexyl or 8-nitrooctyl and more preferably it includes 5-nitropentyl or 6-nitrohexyl.

In the case where $R^3$ is an unsubstituted aryl group, a preferable aryl group is a phenyl group or a naphthyl group.

In the case where $R^3$ is a substituted aryl group, said aryl group has a substituent selected from the group consisting of a halogen atom, a cyano group, a hydroxy group, a sulfonic acid group, a substituted or unsubstituted alkyl group, a carboxy group, an alkoxycarbonyl group, a carbamoyl group, an alkoxy group, a phenoxy group and a nitro group.

The above halogen atom includes a fluorine atom, a chlorine atom, a bromine atom, an iodine atom and the like, and a chlorine atom is preferable.

In the case where $R^3$ is an aryl group having a halogen atom, specific examples thereof include 2-chlorophenyl, 4-chlorophenyl, 2-bromophenyl, 4-bromophenyl, 2-iodophenyl, 2-fluorophenyl, 2-chloronaphthyl, 4-chloronaphthyl, 2-bromonaphthyl, 4-iodonaphthyl, 4-bromonaphthyl, 2-fluoronaphthyl, 4-fluoronaphthyl and the like.

In the case where $R^3$ is an aryl group having a hydroxy group, specific examples thereof include 2-hydroxyphenyl, 4-hydroxyphenyl, 2-hydroxynaphthyl, 4-hydroxynaphthyl and the like.

In the case where $R^3$ is an aryl group having a sulfonic acid group, specific examples thereof include 2-sulfophenyl, 3-sulfophenyl, 4-sulfophenyl, 2-sulfonaphthyl, 3-sulfonaphthyl, 4-sulfonaphthyl, 5-sulfonaphthyl, 8-sulfonaphthyl and the like. A phenyl group having a sulfonic acid group as a substituent is more preferable.

In the case where $R^3$ is an aryl group having a substituted or unsubstituted alkyl group, said alkyl group is more preferably unsubstituted. Specific examples of the aryl group having said alkyl group include 2-methylphenyl, 4-methylphenyl, 2,4-dimethylphenyl and the like.

In the case where $R^3$ is an aryl group having a carboxy group, specific examples thereof include 2-carboxyphenyl, 4-carboxyphenyl, 2-carboxynaphthyl, 4-carboxynaphthyl and the like. A phenyl group having a carboxy group as a substituent is more preferable.

In the case where $R^3$ is an aryl group having an alkoxycarbonyl group, specific examples thereof include 2-methoxycarbonylphenyl, 4-methoxycarbonylphenyl, 2-ethoxycarbonylphenyl, 4-ethoxycarbonylphenyl, 4-butoxycarbonylphenyl, 2-methoxycarbonylnaphthyl and the like.

In the case where $R^3$ is an aryl group having a carbamoyl group, specific examples thereof include 2-carbamoylphenyl, 4-carbamoylphenyl, 2-carbamoylnaphthyl, 4-carbamoylnaphthyl and the like.

In the case where $R^3$ is an aryl group having an alkoxy group, specific examples thereof include 2-methoxyphenyl, 4-methoxyphenyl, 2-ethoxyphenyl, 4-ethoxyphenyl, 2-butoxyphenyl, 2-methoxynaphthyl, 4-ethoxynaphthyl and the like.

In the case where $R^3$ is an aryl group having a phenoxy group, specific examples thereof include 2-phenoxyphenyl, 4-phenoxyphenyl, 4-phenoxynaphthyl, 5-phenoxynaphthyl and the like.

In the case where $R^3$ is an aryl group having a nitro group, specific examples thereof include 2-nitrophenyl, 3-nitrophenyl, 4-nitrophenyl, 2-nitronaphthyl, 4-nitronaphthyl, 8-nitronaphthyl and the like.

In the case where $R^3$ is an unsubstituted heteroaryl group, a preferable heteroaryl group is a 2-, 3- or 4-pyridyl group.

In the case where $R^3$ is a substituted heteroaryl group, said heteroaryl group has a substituent selected from the group consisting of a halogen atom, a cyano group, a hydroxy group, a sulfonic acid group, a substituted or unsubstituted alkyl group, a carboxy group, an alkoxycarbonyl group, a carbamoyl group, an alkoxy group, a phenoxy group and a nitro group.

In the case where $R^3$ is a heteroaryl group having a halogen atom, said halogen atom may be the same as in the above case where $R^3$ is a substituted aryl group.

In the case where $R^3$ is a heteroaryl group having a halogen atom, specific examples thereof include 4-chloro-2-pyridyl, 6-chloro-2-pyridyl, 4-bromo-2-pyridyl, 6-bromo-2-pyridyl, 4-fluoro-2-pyridyl, 6-fluoro-2-pyridyl, 4-iodo-2-pyridyl, 6-iodo-2-pyridyl, 2-chloro-4-pyridyl, 2-bromo-4-pyridyl, 2-iodo-4-pyridyl, 2-fluoro-4-pyridyl and the like.

In the case where $R^3$ is a heteroaryl group having a hydroxy group, specific examples thereof include 4-hydroxy-2-pyridyl, 6-hydroxy-2-pyridyl, 2-hydroxy-4-pyridyl and the like.

In the case where $R^3$ is a heteroaryl group having a sulfonic acid group, specific examples thereof include 4-sulfo-2-pyridyl, 6-sulfo-2-pyridyl, 2-sulfo-4-pyridyl and the like.

In the case where $R^3$ is a heteroaryl group having a substituted or unsubstituted alkyl group, said alkyl group is preferably unsubstituted, and specific examples thereof include 4-methyl-2-pyridyl, 5-methyl-3-pyridyl, 6-methyl-4-pyridyl and the like.

In the case where $R^3$ is a heteroaryl group having a carboxy group, specific examples thereof include 4-carboxy-2-pyridyl, 6-carboxy-3-pyridyl, 6-carboxy-2-pyridyl and the like.

In the case where $R^3$ is a heteroaryl group having an alkoxycarbonyl group, specific examples thereof include 4-methoxycarbonyl-2-pyridyl, 6-methoxycarbonyl-3-pyridyl, 6-ethoxycarbonyl-2-pyridyl and the like.

In the case where $R^3$ is a heteroaryl group having a carbamoyl group, specific examples thereof include 4-carbamoyl-2-pyridyl, 6-carbamoyl-3-pyridyl, 6-carbamoyl-4-pyridyl and the like.

In the case where $R^3$ is a heteroaryl group having an alkoxy group, specific examples thereof include 4-methoxy-2-pyridyl, 6-butoxy-3-pyridyl, 6-ethoxy-4-pyridyl and the like.

In the case where $R^3$ is a heteroaryl group having a phenoxy group, specific examples thereof include 4-phenoxy-2-pyridyl, 6-phenoxy-3-pyridyl, 6-phenoxy-4-pyridyl and the like.

In the case where $R^3$ is a heteroaryl group having a nitro group, specific examples thereof include 4-nitro-2-pyridyl, 6-nitro-3-pyridyl, 6-nitro-4-pyridyl and the like.

$R^3$ in the formula (1) is preferably an unsubstituted C5-C12 alkyl group, a substituted C5-C12 alkyl group having the above substituent, an unsubstituted aryl group or a substituted aryl group having the above substituent. It is more preferably an unsubstituted C5-C12 alkyl group or a carboxy-substituted aryl group, and further preferably an unsubstituted C6-C8 alkyl group or a carboxy-substituted aryl group. In some cases, it is more preferably an unsubstituted C6-C8 alkyl group; a substituted C6-C8 alkyl group having, as a substituent, a group selected from the group consisting of an aryl group, a heterocyclic group, a sulfonic acid group, a carboxy group, an alkoxycarbonyl group, an acyl group, a carbamoyl group, a cyano group, an alkoxy group, a phenoxy group, a hydroxy group and a nitro group; or a substituted phenyl group having, as a substituent, a sulfonic acid group or a carboxy group. It is particularly preferably a straight-chain unsubstituted C6 alkyl group or a carboxy-substituted phenyl group.

In the formula (1), with regard to the substitution positions of —$SO_2R^3$ and —$SO_3H$ whose substitution position are not specified and the both of which the benzene ring has thereon, one of their substitution positions is the para-position and the other thereof is the ortho-position to the substitution position of the nitrogen atom by which said benzene ring is substituted.

With regard to $R^1$ to $R^3$ in the above formula (1), a compound in combination of preferable ones is more preferably, and a compound in combination of more preferable ones therefor is further preferable. The same is true in a compound in combination of particularly preferable ones.

Specifically, preferable anthrapyridone compounds are as followed.

The compound (i) corresponding to Claim 3 can include an anthrapyridone compound where, in the above formula (1), $R^1$ is a hydrogen atom or methyl, $R^2$ is a hydrogen atom or methoxy and $R^3$ is an unsubstituted C6-C8 alkyl group; a substituted C6-C8 alkyl group having, as a substituent, a group selected from the group consisting of an aryl group, a heterocyclic group, a sulfonic acid group, a carboxy group, an alkoxycarbonyl group, an acyl group, a carbamoyl group, a cyano group, an alkoxy group, a phenoxy group, a hydroxy group and a nitro group; or a substituted phenyl group having, as a substituent, a sulfonic acid group or a carboxy group, the compound (ii) in combination of more preferable ones can include an anthrapyridone compound where, in the above (i), $R^3$ is an unsubstituted C5-C12 alkyl group or a carboxy-substituted aryl group, the compound (iii) in combination of particularly preferable ones can include an anthrapyridone compound where, the above (i), $R^1$ is methyl and $R^3$ is a straight-chain unsubstituted C6 alkyl group or a carboxy-substituted phenyl group.

A salt of the compound of the above formula (1) is a salt which the compound of the above formula (1) forms with an inorganic or organic base. Said salt is preferably a salt with an inorganic base, such as an alkali metal salt (for example, a lithium salt, a sodium salt or a potassium salt) or an ammonium salt; or a salt with an organic base, such as a quaternary ammonium salt represented by the following formula (2).

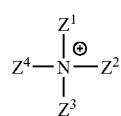

(2)

[Wherein, $Z^1$ to $Z^4$ each independently represent an alkyl group, a hydroxy alkyl group or a hydroxyalkoxyalkyl group.]

Specific examples of $Z^1$ to $Z^4$ in the formula (2) include the following groups. Examples of the alkyl group include lower alkyl groups such as methyl or ethyl; examples of the hydroxy alkyl group include hydroxy lower alkyl groups such as hydroxymethyl, 2-hydroxyethyl, 3-hydroxypropyl, 2-hydroxypropyl, 4-hydroxybutyl, 3-hydroxybutyl or 2-hydroxybutyl; and examples of the hydroxyalkoxyalkyl group include hydroxy lower alkoxy lower alkyl groups such as hydroxyethoxymethyl, 2-hydroxyethoxyethyl, 3-hydroxyethoxypropyl, 3-hydroxyethoxybutyl or 2-hydroxyethoxybutyl.

Among the above salts of the compound of formula (1), more preferable one includes each salt formed with sodium, potassium, lithium, monoethanolamine, diethanolamine, triethanolamine, monoisopropanolamine, diisopropanolamine, triisopropanolamine, ammonium or the like. Among them, particularly preferable one is each salt formed with lithium, ammonium and sodium.

A method for producing the above salt will be described.

For example, it is possible to obtain a sodium salt of the compound of the formula (1) as a wet cake by salting out by adding sodium chloride to a reaction liquid containing a compound of the above formula (1) or to an aqueous solution containing a compound of the formula (1) where a wet cake or a dried form of a compound of the formula (1) is dissolved in water, and by separating by filtration of the precipitate. In addition, it is possible to obtain a compound represented by the formula (1) as a wet cake in free acid form by again dissolving the obtained wet cake in water followed by adding hydrochloric acid to adjust the pH to a strong acidic (usually, pH 1 to 2 or less) condition, and by separating by filtration of the resulting crystals. Alternatively, it is also possible to obtain a mixture of sodium salt and free acid in a desired ratio by appropriately adjusting the pH with sodium hydroxide. Further, it is possible to obtain a corresponding potassium, lithium, ammonium or quaternary ammonium salt thereof by adding a wet cake of the above free acid to water and by adding, for example, potassium hydroxide, lithium hydroxide, ammonia water, a quaternary ammonium salt represented by the above formula (2), or the like to make it alkaline. In this case, it is also possible to obtain a mixed salt of sodium and potassium, a mixture of a sodium salt, a potassium salt and free acid, or the like by using, for example, a wet cake of a mixture of free acid and a sodium salt, and by adding potassium hydroxide. Among these salts, particularly preferable ones are salts of lithium, ammonium and sodium as described above.

Specific examples of the anthrapyridone compound represented by the above formula (1) of the present invention will be shown in Table 1. In the formula (1), with regard to the substitution positions of —$SO_2R^3$ (sulfonyl group having $R^3$) and —$SO_3H$ (sulfonic acid group) whose substitution position are not specified and the both of which the benzene ring has thereon, one of their substitution positions is the para-position and the other thereof is the ortho-position to the substitution position of the nitrogen atom by which said benzene ring is substituted, as described above. Accordingly, as "the substitution position of the sulfonyl group", the position of only the former is denoted. Further, In Table 1, "o,p-sulfophenyl" for the compound No. 5 means that it is a mixture of two compounds, an o-sulfophenyl derivative and a p-sulfophenyl derivative.

TABLE 1

| No. | R1 | R2 | Substitution position of sulfonyl group | R3 |
| --- | --- | --- | --- | --- |
| 1 | CH3 | H | Para | n-Hexyl |
| 2 | CH3 | OMe | Para | n-Hexyl |
| 3 | CH3 | H | Para | 2-Ethylhexyl |
| 4 | CH3 | H | Para | n-Pentyl |
| 5 | CH3 | H | Para | o,p-Sulfophenyl |
| 6 | CH3 | H | Para | o-Carboxyphenyl |
| 7 | CH3 | OMe | Para | o-Carboxyphenyl |
| 8 | CH3 | H | Para | n-Octyl |
| 9 | CH3 | H | Para | n-Decyl |
| 10 | CH3 | H | Para | n-Undecyl |
| 11 | CH3 | H | Para | n-Dodecyl |
| 12 | CH3 | OMe | Para | n-Pentyl |
| 13 | CH3 | OMe | Para | Isopentyl |
| 14 | CH3 | H | Ortho | n-Hexyl |

TABLE 1-continued

| No. | R1 | R2 | Substitution position of sulfonyl group | R3 |
|---|---|---|---|---|
| 15 | CH3 | OMe | Ortho | n-Hexyl |
| 16 | CH3 | H | Ortho | n-Pentyl |
| 17 | CH3 | H | Ortho | 2-Ethylhexyl |
| 18 | CH3 | H | Ortho | n-Octyl |
| 19 | CH3 | H | Ortho | n-Decyl |
| 20 | CH3 | OMe | Ortho | n-Undecyl |
| 21 | CH3 | H | Ortho | n-Dodecyl |
| 22 | CH3 | H | Ortho | Isopentyl |
| 23 | CH3 | H | Ortho | Tert-pentyl |
| 24 | CH3 | H | Ortho | Neopentyl |
| 25 | CH3 | H | Ortho | Isohexyl |
| 26 | CH3 | OMe | Ortho | Isohexyl |
| 27 | CH3 | H | Para | Isohexyl |
| 28 | CH3 | H | Para | Isopentyl |
| 29 | CH3 | H | Para | Neopentyl |
| 30 | CH3 | H | Para | Tert-pentyl |

Hereinafter, the method for producing the anthrapyridone compound of the present invention will be described. In this regard, $R^1$ to $R^3$ in the following formulas (3) to (6) have the same meanings as in the above formula (1).

The anthrapyridone compound of the present invention is produced by, for example, the following method. That is, 1 mol of an anthraquinone compound shown in the following formula (3) is reacted with 1.1 to 3 mol of ethyl benzoylacetate or its derivative having $R^2$ as a substituent in a polar solvent such as xylene, in the presence of a basic compound such as sodium carbonate at 130 to 180° C. for 5 to 15 hours, whereby a compound of the following formula (4) is obtained, Formula (3)

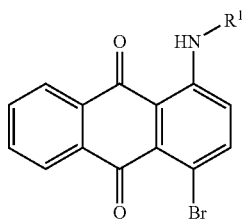

(3)

Then, 1 mol of the obtained compound of the above formula (4) is reacted (Ullmann reaction: condensation) with 1 to 5 mol of a para- (or ortho-) aminophenylalkylthio ether compound, a para- (or ortho-) aminophenylarylthio ether compound, or a para- (or ortho-) aminophenylheteroarylthio ether compound in an aprotic polar organic solvent such as N,N-dimethylformamide in the presence of a base like sodium carbonate and a copper catalyst like copper acetate at 110 to 150° C. for 2 to 6 hours, whereby a compound of the following formula (5) is obtained.

Formula (5)

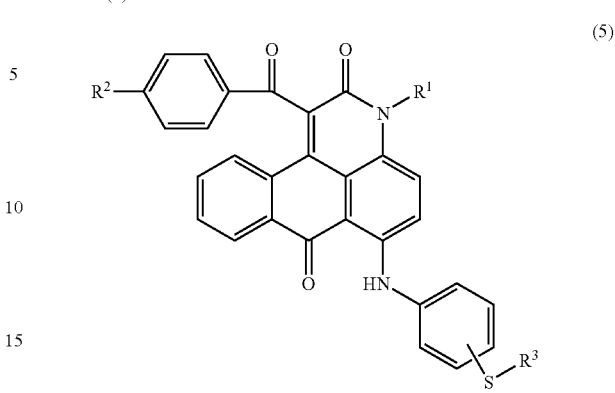

(5)

[Wherein, $R^3$—S group whose substitution position is not specified is substituted on either the ortho-position or the para-position on the benzene ring.]

Then, the obtained compound of the above formula (5) is placed in acetic acid and oxidized by dropwise-addition of hydrogen peroxide at 50 to 80° C. (oxidation of a sulfur atom in thio ether group) to obtain an anthrapyridone compound of the following formula (6).

Formula (6)

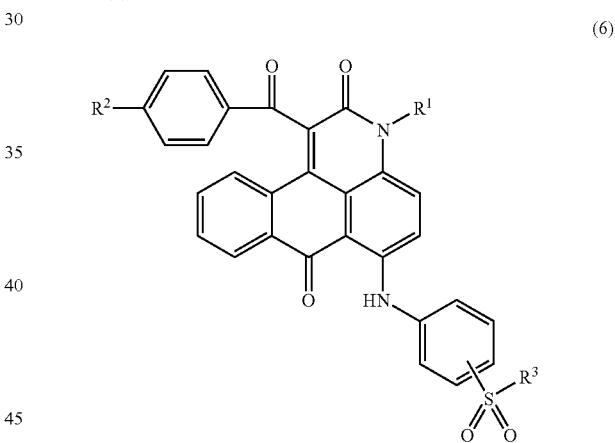

(6)

[Wherein, the sulfonyl group having $R^3$ whose substitution position is not specified is substituted on either the ortho-position or the para-position on the benzene ring.]

Then, the obtained compound of the above formula (6) is sulfonated in 5 to 15% fuming sulfuric acid by a conventional method. After that, the reaction liquid is added by pouring to ice water, aciding out, salting out or the like is further carried out and the precipitated solid is separated by filtration, whereby an anthrapyridone compound represented by the above formula (1) of the present invention is obtained. In this regard, in the formula (6), the para-position is subjected to sulfonation when a sulfonyl group having $R^3$ is substituted on the ortho-position of the benzene ring, and the ortho-position is subjected to sulfonation when said sulfonyl group is substituted on the para-position.

It is possible to obtain the compound of the above formula (1) in free acid form or its salt form. The anthrapyridone compound of the present invention is used as a coloring matter for ink or the like in a form such as free acid or a salt thereof, for example, an alkali metal salt, an alkaline earth metal salt, an alkyl amine salt, an alkanolamine salt or an ammonium salt. The method for producing free acid from various salts, and the method for producing various salts or various mixed salts from free acid, mixtures of free acid and a salt, or the like are as described above.

The compound represented by the above formula (1) is preferably a compound with a less amount of inorganic impurities such as chloride and sulfate of a metal contained as impurity in the total mass of said compound. The content thereof is, for example, approximately 1% by mass or less only as a guide. In order to produce an anthrapyridone compound of the present invention with less inorganic impurity, the above-obtained compound of the present invention may be subjected to desalting treatment by an ordinary method using, for example, a reverse osmosis membrane.

The ink composition of the present invention contains a compound represented by the above formula (1) of the present invention or a salt thereof as a coloring matter component, and it can be obtained by dissolving said compound in water or an aqueous solvent (the later-described water containing a water-soluble organic solvent), according to necessity, together with an ink preparation agent and the like. For example, a reaction liquid containing a compound represented by the above formula (1) can be directly used for production of an ink composition of the present invention. In addition, it is also possible that a compound of the formula (1) is separated by crystallization from the above reaction liquid or by spray-drying the reaction liquid or the like, the resulting dried form of said compound of the formula (1) is used for production of an ink composition. The ink composition of the present invention contains usually 0.1 to 20% by mass, more preferably 1 to 15% by mass and further preferably 2 to 10% by mass of the compound of the present invention. The ink composition of the present invention may contain 0 to 30% by mass of a water-soluble organic solvent and 0 to 5% by weight of an ink preparation agent, respectively. A water-soluble organic solvent is preferably contained. The rest is water.

The usable water-soluble organic solvent includes, for example, C1-C4 alkanols such as methanol, ethanol, n-propanol, isopropanol, n-butanol, isobutanol, secondary butanol or tertiary butanol; carboxylic acid amides such as N,N-dimethylformamide or N,N-dimethylacetoamide; heterocyclic ureas such as 2-pyrrolidone, N-methyl-2-pyrrolidone, 1,3-dimethylimidazolidin-2-one or 1,3-dimethylhexahydropyrimid-2-one; ketones or keto alcohols such as acetone, methyl ethyl ketone or 2-methyl-2-hydroxypentan-4-one; cyclic ethers such as tetrahydrofuran or dioxane; mono-, oligo- or polyalkylene glycols or thioglycols having a C2-C6 alkylene unit such as ethylene glycol, 1,2- or 1,3-propylene glycol, 1,2- or 1,4-butylene glycol, 1,6-hexylene glycol, diethylene glycol, triethylene glycol, tetraethylene glycol, dipropylene glycol, thiodiglycol, polyethylene glycol or polypropylene glycol; polyols (preferably, triol) such as glycerine, hexane-1,2,6-triol; C1-C4 alkyl ethers of polyhydric alcohol, such as ethylene glycol monomethyl ether, ethylene glycol monoethyl ether, diethylene glycol monomethyl ether, diethylene glycol monoethyl ether, diethylene glycol monobutyl ether, triethylene glycol monomethyl ether or triethylene glycol monoethyl ether; gamma-butyrolactone or dimethylsulfoxide; and the like.

Among the above, preferable are isopropanol, glycerine, mono-, di- or triethylene glycol, dipropylene glycol, 2-pyrrolidone, N-methyl-2-pyrrolidone and/or diethylene glycol monobutyl ether and more preferable are isopropanol, glycerine, diethylene glycol monobutyl ether (butyl carbitol), 2-pyrrolidone and/or N-methyl-2-pyrrolidone. These water-soluble organic solvents are used alone or as a mixture thereof.

Hereinafter, the usable ink preparation agent in preparation of the ink composition of the present invention will be explained. Specific examples of the ink preparation agent include, for example, an antiseptic and fungicide, a pH adjuster, a chelating agent, a rust preventive agent, a water-soluble UV absorbing agent, a water-soluble polymer compound, a dye dissolving agent, a surfactant and the like.

The antiseptic and fungicide includes, for example, organic sulfur-based, organic nitrogen sulfur-based, organic halogen-based, haloallylsulfone-based, iodopropargyl-based, N-haloalkylthio-based, nitrile-based, pyridine-based, 8-oxyquinoline-based, benzothiazole-based, isothiazoline-based, dithiol-based, pyridineoxide-based, nitropropane-based, organic tin-based, phenol-based, quaternary ammonium salt-based, triazine-based, thiadiazine-based, anilide-based, adamantane-based, dithiocarbamate-based, brominated indanone-based and benzyl bromoacetate-based compounds.

The organic halogen-based compound includes, for example, sodium pentachlorophenol.

The pyridineoxide-based compound includes, for example, sodium 2-pyridinethiol-1-oxide.

The isothiazoline-based compound includes, for example, 1,2-benzo isothiazolin-3-one, 2-n-octyl-4-isothiazolin-3-one, 5-chloro-2-methyl-4-isothiazolin-3-one, 5-chloro-2-methyl-4-isothiazolin-3-one magnesium chloride, 5-chloro-2-methyl-4-isothiazolin-3-one calcium chloride, 2-methyl-4-isothiazolin-3-one calcium chloride or the like.

In addition, the other antiseptic and fungicide includes sodium sorbate, sodium benzoate, anhydrous sodium acetate and the like.

In this regard, the antiseptic and fungicide where 1,2-benzo isothiazolin-3-one is an effective component includes, for example, Proxel® GXL(S) and Proxel® XL-2(S) (which are trade names and all of which are manufactured by Avecia Corp.) and the like.

As the pH adjuster, any substance can be used as long as it can control the pH of ink in the range of 7.5 to 11.0 without any adverse effect on an intended ink. It includes, for example, alkanolamines such as diethanolamine and triethanolamine, hydroxides of alkali metals such as lithium hydroxide, sodium hydroxide and potassium hydroxide, ammonium hydroxide, or alkali metal carbonates such as lithium carbonate, sodium carbonate and potassium carbonate.

The chelating agent includes, for example, sodium ethylenediaminetetraacetate, sodium nitrilotriacetate, sodium hydroxyethylethylenediaminetriacetate, sodium diethylenetriaminepentaacetate, sodium uracil diacetate and the like.

The rust preventive agent includes, for example, hydrogen sulfite salts, sodium thiosulfate, ammonium thioglycolate, diisopropylammonium nitrite, pentaerythritol tetranitrate, dicyclohexylammonium nitrite and the like.

The water-soluble UV absorbing agent includes, for example, sulfonated benzophenone, sulfonated benzotriazole and the like.

The water-soluble polymer compound includes, for example, polyvinyl alcohol, cellulose derivatives, polyamine, polyimines and the like.

The dye dissolving agent includes, for example, urea, epsilon-caprolactam, ethylene carbonate and the like.

The surfactant includes, for example, an anionic surfactant, an amphoteric surfactant, a cationic surfactant, a nonionic surfactant and the like.

The anionic surfactant includes alkylsulfocarboxylate, alpha-olefin sulfonate, polyoxyethylene alkyl ether acetate, N-acylamino acid and salts thereof, N-acylmethyltaurine salts, alkylsulfate polyoxyalkyl ether sulfate, alkylsulfate polyoxyethylene alkyl ether phosphate, rosin acid soap, castor oil sulfate, lauryl alcohol sulfate, alkylphenol type phosphate ester, alkyl type phosphate ester, alkylaryl sulfonate, diethyl sulfosuccinate, diethylhexyl sulfosuccinate, dioctyl sulfosuccinate and the like.

The cationic surfactant includes 2-vinylpyridine derivatives, poly(4-vinylpyridine) derivatives and the like.

The amphoteric surfactant includes lauryldimethylaminoacetic acid betaine, 2-alkyl-N-carboxymethyl-N-hydroxyethyl imidazolinium betaine, coconut oil fatty acid amide propyldimethylaminoacetic acid betaine and polyoctylpolyaminoethylglycine, and in addition, imidazoline derivatives and the like.

The nonionic surfactant includes ether type such as polyoxyethylene nonylphenyl ether, polyoxyethylene octylphenyl ether, polyoxyethylene dodecylphenyl ether, polyoxyethylene oleyl ether, polyoxyethylene lauryl ether and polyoxyethylene alkyl ether; ester type such as polyoxyethylene oleate ester, polyoxyethylene distearate ester, sorbitan laurate, sorbitan monostearate, sorbitan monooleate, sorbitan sesquioleate, polyoxyethylene monooleate and polyoxyethylene stearate; acetylene alcohol type surfactants such as 2,4,7,9-tetramethyl-5-decyne-4,7-diol, 3,6-dimethyl-4-octyne -3,6-diol and 3,5-dimethyl-1-hexyn-3-ol. Other specific examples include Surfynol® 104E, 104PG50, 82 and 465, and Olfine® STG (which are trade names and all of which are manufactured by Nissin Chemical Industry Co., Ltd.). These ink preparation agents are used alone or as a mixture thereof.

The ink composition of the present invention is a water-based ink composition and can be produced by dissolving the anthrapyridone compound of the present invention represented by the above formula (1) or a salt thereof (hereinafter, also referred to as the present compound) in water or the above aqueous solvent (water containing a water-soluble organic solvent), according to necessity, together with the above ink preparation agent and the like.

In the above method, the order of dissolving the components is not particularly limited. The present compound may be dissolved in water or the above aqueous solvent in advance, followed by addition of an ink preparation agent, or the present compound may be dissolved in water, followed by addition of an aqueous solvent and an ink preparation agent. Or the order may be different from this. Otherwise, a water-soluble organic solvent, an ink preparation agent and the like may be added to a reaction liquid containing the present compound or a solution of the present compound subjected to desalting treatment using a reverse osmosis membrane, to produce an ink composition. Water to be used in preparation of said ink composition is preferably water with less impurity, such as ion-exchanged water or distilled water. Further, microfiltration may be carried out, according to necessity, using a membrane filter, in order to remove foreign substances. Particularly when it is used as an ink for inkjet printer, it is preferred to carry out microfiltration. The pore size of filter to carry out microfiltration is usually 1 to 0.1 μm and preferably 0.8 to 0.2 μm.

The colored product of the present invention means a material colored with the present compound. The material to be colored is not particularly limited and includes, for example, paper, fiber and cloth (such as cellulose, nylon and wool), leather, substrates for color filters, and the like, but not limited thereto. The coloration includes, for example, printing methods such as dip dyeing, textile printing and screen printing, inkjet recording methods using an inkjet printer, and the like. In the present invention, an inkjet recording method is preferable.

The record-receiving material (media) applicable to the inkjet recording method of the present invention includes, for example, communication sheets such as paper or film, fiber, leather and the like. The communication sheet is preferably a sheet subjected to surface treatment, specifically a sheet provided with an ink receiving layer on a substrate of, for example, the above record-receiving material or the like. Said ink receiving layer is provided by, for example, impregnating or coating a substrate with a cation polymer; coating the surface of a substrate with a porous white inorganic substance which can absorb the coloring matter in ink, such as porous silica, aluminasol and special ceramics, together with a hydrophilic polymer such as polyvinyl alcohol and polyvinyl pyrrolidone; and the like. The sheet provided with such an ink receiving layer is called usually inkjet professional paper (film), glossy paper (film) or the like. Specific products include, for example, Pictorico® Pro (which is manufactured by Pictorico); Professional Photopaper, Super Photopaper and Matte Photopaper (which are all manufactured by Canon Inc.); CRISPIA®, Photo Paper (glossy), Photo Matte Paper and Super Fine Glossy Film (which are all manufactured by Seiko-Epson Corporation); Advanced Photo Paper, Premium Plus Photo Paper, Premium Glossy Film and Photo Paper (which are all manufactured by Hewlett Packard Japan, Ltd.); PhotoLike® QP (which is manufactured by Konica Minolta Photo Imaging, Inc.); and the like. In this regard, plain paper is also obviously a record-receiving material applicable to the recording method of the present invention.

Among them, it is known that discoloration or fading by ozone gas is particularly developed in images recorded on a record-receiving material whose surface is coated with a porous white inorganic substance. The water-based magenta ink composition of the present invention is excellent in fastness to gases including ozone gas, so it has particularly great effect in recording on such a record-receiving material.

The above porous white inorganic substance includes calcium carbonate, kaolin, talc, clay, diatom earth, synthesized amorphous silica, aluminum silicate, magnesium silicate, calcium silicate, aluminum hydroxide, alumina, lithopone, zeolite, barium sulfate, calcium sulfate, titanium dioxide, zinc sulfide, zinc carbonate and the like.

In order that recording is performed on a record-receiving material by the inkjet recording method of the present invention, for example, a container containing an ink composition of the present invention is placed in the predetermined position in an inkjet printer and recording may be performed on a record-receiving material by an ordinary method. In the inkjet recording method of the present invention, the magenta ink composition of the present invention may be used alone, or said magenta ink composition and ink compositions such as yellow, cyan, green, orange, blue (or violet), and according to necessity, with black and the like may be used in combination. Each ink composition to be used in combination is filled into each container, and these containers are placed (loaded) in the predetermined positions in an inkjet printer likewise the container containing a magenta ink composition for inkjet recording of the present invention and used in inkjet-printing together with the ink composition of the present invention. The inkjet printer includes, for example, a printer of piezo inkjet using mechanical vibration; a printer of Bubble Jet® utilizing bubbles generated by heating; and the like.

The ink composition of the present invention is vivid magenta, exhibits highly vivid hue particularly on inkjet glossy paper, and further has high fastness on recorded images. In addition, it is also safe to human beings.

The ink composition of the present invention is free from precipitation and separation during storage. In addition, when the ink composition of the present invention is used in inkjet recording, it doesn't cause clogging of an injector (inkhead). The ink composition of the present invention is free from changes in physical properties even in intermittent use by a continuous inkjet printer.

EXAMPLES

The present invention will be further specifically explained below with reference to Examples. "Part(s)" and "%" in the description are based mass unless otherwise specified. Manipulations such as each reaction and crystallization are carried out under stirring unless otherwise specifically noted.

Any of the synthesized compounds of the present invention showed a solubility of more than 100 g/L in water.

In addition, the maximum absorption wavelength (λmax) of each compound in Examples is a value measured in an aqueous solution unless otherwise specifically noted. With regard to the purity of the anthrapyridone compound of the present invention obtained in each Example, its area ratio determined using HPLC is denoted as purity. The analysis equipment and the analysis conditions are as follows.

Equipments used for HPLC and measurement conditions:
Apparatus; trade name: HP1100 (manufactured by Agilent Technology)
Column; trade name: Inertsil ODS-2 (5 μm)
  1.6×250 mm (manufactured by GL Sciences Inc.)
Column temperature; 40° C.
Mobile phase; A: 5 mM AcONH$_4$, B: CH$_3$CN
Gradient; Bconc. 10%-(30 min)-60%
Flow rate; 0.8 ml/min
Measurement wavelength; 254 nm Example 1

(1)
To 360 parts of xylene, 94.8 parts of a compound represented by the above formula (3) where R$^1$ is methyl, 3.0 parts of sodium carbonate and 144.0 parts of ethyl benzoylacetate were sequentially added, and the liquid temperature was raised to 140 to 150° C. At this temperature, the reaction was carried out for 8 hours, and meantime ethanol and water produced during the reaction were distilled out of the system as a xylene azeotrope to complete the reaction. After the resulting reaction liquid was cooled to 30° C. and 240 parts of methanol were added thereto followed by stirring for 30 minutes, the precipitated solid was separated by filtration. The obtained solid was washed with 360 parts of methanol and then dried, whereby 124.8 parts of a compound represented by the above formula (4) where R$^1$ was CH$_3$ and R$^2$ was H were obtained as pale yellow needle crystals.

(2)
Next, after 111 parts of a compound obtained in (1) of the present Example, 104.5 parts of para-aminophenyl-n-hexylthio ether, 30.0 parts of copper (II) acetate monohydrate and 30.8 parts of sodium acetate were sequentially added to 500.0 parts of N,N-dimethylformamide and the liquid temperature was raised to 130 to 135° C. over 1 hour, the reaction was carried out at this temperature for 3 hours. After the reaction liquid was cooled to about 60° C., 250 parts of methanol were added thereto, the mixture was further cooled to room temperature, and the precipitated solid was separated by filtration. The obtained solid was sequentially washed with 125 parts of N,N-dimethylformamide, 500 parts of methanol and then hot water of 80° C. followed by drying, whereby 122.7 parts of a compound represented by the above formula (5) where R$^1$ was CH$_3$, R$^2$ was H, R$^3$ was n-hexyl and the substitution position of the thio ether group having R$^3$ was the para-position on the benzene ring were obtained as bluish red crystals.

(3)
Next, to 1000 parts of acetic acid and 5 parts of sodium tungstate dihydrate, 102.7 parts of a compound of the formula (5) obtained in the above (2) were added at 60° C. or less, and the liquid temperature was raised to 75 to 80° C. At this temperature, 40 parts of a 30% hydrogen peroxide solution were added dropwise to said reaction liquid over 1.5 hours, and the reaction was further carried out for 5 hours. To the resulting reaction liquid, 300 parts of methanol were added dropwise at a liquid temperature of 65 to 70° C. for 30 minutes. After the liquid temperature was cooled to 30° C., the precipitated solid was separated by filtration. The obtained solid was washed with water and dried, whereby 104 parts of a compound represented by the above formula (6) where R$^1$ was CH$_3$, R$^2$ was H, R$^3$ was n-hexyl and the substitution position of the sulfonyl group having R$^3$ was the para-position on the benzene ring were obtained as red crystals.

(4)
Next, to 217.8 parts of 96.0% sulfuric acid, 342.2 parts of 30.5% fuming sulfuric acid were added under water-cooling to prepare 560 parts of 10% fuming sulfuric acid. Thereto, 93 parts of the compound of the formula (6) obtained in the above (3) were added at a liquid temperature of 50° C. or less, under water-cooling. The liquid temperature was raised to 60 to 65° C. and the reaction was carried out at this temperature for 5 hours. Next, to 1300 parts of ice water, the above-obtained reaction liquid was added, and water was added to adjust the whole liquid volume to 3000 parts. The resulting liquid was heated to 60° C. over 30 minutes, followed by filtration to remove insoluble matter. The mother liquid was left to cool to room temperature, and the precipitated solid was separated by filtration. The obtained solid was washed with 300 parts of a 20% aqueous ammonium chloride solution to obtain 156 parts of a wet cake of a compound represented by the following formula (7) (Compound No. 1 in the above Table 1) as red crystals. After the obtained wet cake was added to 1000 parts of ethanol and the mixture was stirred at 60° C. for 30 minutes, the precipitated solid was separated by filtration. The obtained wet cake was dried to obtain 87.0 parts of a compound of the present invention represented by the following formula (7) where the inorganic salt content was 1% by mass or less, as dark red crystals.

λmax: 523 nm, HPLC purity: 96.9%.

(7)

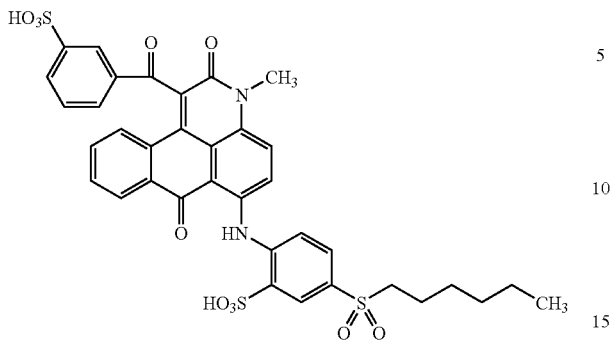

(8)

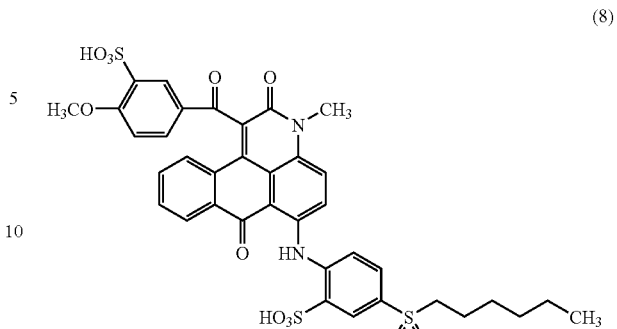

Synthesis Example 1

Para-aminophenyl-n-hexylthio ether used in Example 1 (2) was synthesized by the following method.

After 102.5 parts of p-chloronitrobenzene and 50 parts of potassium carbonate were added to 250 parts of N,N-dimethylformamide, 105 parts of n-hexylmercaptan were added dropwise while maintaining the liquid temperature at 50° C. or less. After the liquid temperature was raised to 95 to 105° C., the reaction was carried out at this temperature for 3 hours. The reaction liquid was cooled and then added by pouring to 1000 parts of ice water. The precipitated solid was separated by filtration and washed with cold water followed by drying under reduced pressure, whereby 150 parts of para-nitrophenyl-n-hexylthio ether were obtained. After 150 parts of the obtained para-nitrophenyl-n-hexylthio ether, 10 parts of activated carbon and 1 part of ferric chloride hexahydrate were added to 300 parts of methanol, the liquid temperature was raised to 60 to 65° C. and the mixture was stirred at this temperature for 20 minutes. To the reaction liquid, a mixture of 100 parts of 80% hydrazine monohydrate and 125 parts of methanol were added dropwise over 1 hour while maintaining the liquid temperature at 65° C. or less. After the reaction was carried out at the same temperature for 3 hours, the reaction liquid was filtered to remove insoluble substances. The mother liquid was concentrated, and toluene and an aqueous saturated sodium chloride solution were added for liquid-liquid extraction. After the organic layer was dried with sodium sulfate, the sodium sulfate was removed by filtration. The resulting mother liquid was concentrated under vacuum, whereby 125 parts of para-aminophenyl-n-hexylthio ether were obtained as an oily substance. This compound was used in the reaction in the above Example 1 (2) without further purification.

Example 2

In the same manner as in Example 1 except that ethyl anisoylacetate was used instead of ethyl benzoylacetate used in Example 1 (1), a compound of the present invention represented by the following formula (8) (Compound No. 2 in the above Table 1) was obtained as a dark red solid.

λmax: 520 nm, HPLC purity: 97.6%.

Example 3

In the same manner as in Example 1 except that para-aminophenyl-o-carbethoxyphenylthio ether was used instead of para-aminophenyl-n-hexylthio ether used in Example 1 (2), a compound of the present invention represented by the following formula (9) (Compound No. 6 in the above Table 1) was obtained as a dark red solid.

λmax: 528 nm, HPLC purity: 94%.

(9)

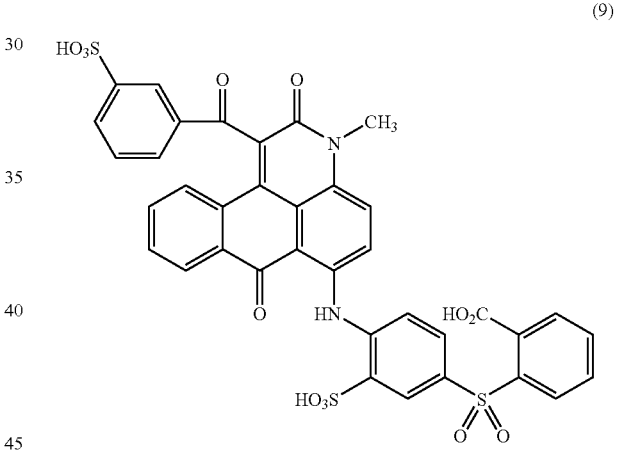

Synthesis Example 2

Para-aminophenyl-o-carbethoxyphenylthio ether used in Example 3 was synthesized by the following method.

After 78.8 parts of p-chloronitrobenzene and 42 parts of potassium carbonate were added to 250 parts of N,N-dimethylformamide, 84.8 parts of thiosalicylic acid were added while maintaining the liquid temperature at 50° C. or less. The liquid temperature was raised to 105 to 115° C. and the reaction was carried out for 4 hours. The reaction liquid was cooled to room temperature and then added by pouring to 1000 parts of ice water, and the precipitated solid was separated by filtration. The obtained solid was washed with water and dried to obtain 125.5 parts of p-nitrophenyl-o-carboxyphenylthio ether.

A mixture of 120 parts of p-nitrophenyl-o-carboxyphenylthio ether, 69.2 parts of thionyl chloride and 3 parts of N,N-dimethylformamide were refluxed at a reflux temperature of 80 to 83° C. for 3 hours. After that, unreacted thionyl chloride was distilled away at the same temperature under reduced pressure. To the reaction liquid after said distillation, 42.3 parts of triethylamine and 350 parts of ethanol were added, and the mixture was reacted at a liquid temperature of 70 to 80° C. The reaction liquid was cooled to room temperature, and the precipitated solid was separated by filtration. The obtained solid was sequentially washed with ethanol and water and then dried to obtain 118.6 parts of para-nitrophenyl-o-carbethoxyphenylthio ether.

To 500 parts of methanol, 115 parts of para-nitrophenyl-o-carbethoxyphenylthio ether, 10 parts of activated carbon and 1 part of ferric chloride hexahydrate were added, and the mixture was stirred at a liquid temperature of 60 to 65° C. for 20 minutes. To this reaction liquid, a mixture of 68 parts of 80% hydrazine monohydrate and 100 parts of methanol were added dropwise over 1 hour while maintaining the liquid temperature at 65° C. or less, and reaction was further carried out at the same temperature for 3 hours. The mother liquid obtained by filtration of the reaction liquid was concentrated and the precipitated solid was washed with water and dried to obtain 95.4 parts of para-aminophenyl-o-carbethoxyphenylthio ether which is the title compound.

Example 4

In the same manner as in Example 1 except that para-aminophenyl-2-ethylhexylthio ether was used instead of para-aminophenyl-n-hexylthio ether in Example 1 (2), a compound of the present invention represented by the following formula (10) (Compound No. 3 in Table 1) was obtained as a dark red solid.

λmax: 523 nm, HPLC purity: 88%.

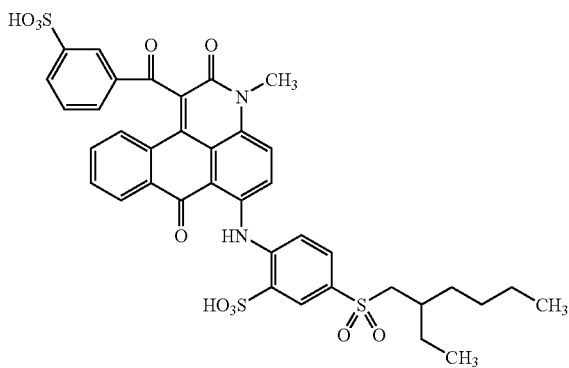

(10)

Synthesis Example 3

Para-aminophenyl-2-ethylhexylthio ether used in Example 4 was synthesized by the following method.

After 19.2 parts of tetrabutyl ammonium bromide and 302 parts of sodium sulfide pentahydrate were added to 370 parts of water, the liquid temperature was raised to 60° C. To this, a solution consisting of 96.1 parts of para-chloronitrobenzene, 118 parts of 2-ethylhexyl bromide and 100.0 parts of toluene was added dropwise over 2 hours while maintaining the reaction liquid at 60° C. or less, and after that, the reaction was carried out at 60 to 65° C. for 3 hours. After the reaction liquid was cooled to room temperature and this was washed by adding toluene and a saturated sodium chloride solution to this, the organic layer was dried with anhydrous sodium sulfate. The filtrate obtained by filtration of the organic layer was concentrated under vacuum and the resulting residue was dried under reduced pressure to obtain 155 parts of para-nitrophenyl-2-ethylhexylthio ether.

To 300 parts of methanol, 150 parts of para-nitrophenyl-2-ethylhexylthio ether, 10 parts of activated carbon and 1 parts of ferric chloride hexahydrate were added, and the mixture was stirred at a liquid temperature of 60 to 65° C. for 20 minutes. To this, a mixture of 65 parts of 80% hydrazine monohydrate and 100 parts of methanol were added dropwise over 1 hour while maintaining the reaction liquid at 65° C. or less, and after that, the reaction was further carried out at the same temperature for 3 hours. The reaction liquid was filtered to remove insoluble matter and the mother liquid was concentrated. After toluene and a saturated sodium chloride solution were added to the resulting residue for washing, the organic layer was dried with anhydrous sodium sulfate. The filtrate obtained by filtration the organic layer was concentrated under vacuum, whereby 125 parts of para-aminophenyl-2-ethylhexylthio ether which was the title compound was obtained.

Examples 5 to 7

(A) Preparation of Ink

Using the compound obtained in Example 1 (Compound No. 1 in Table 1: compound of the formula (7)), an ink composition of the present invention having the composition shown in the following Table 2 was prepared and further filtered using a 0.45 μm membrane filter, whereby an ink for inkjet recording was obtained. In this case, ion-exchanged water was used as water. In this regard, in the preparation of the ink composition, the pH of the ink composition was adjusted to pH=8 to 10 with a 25% aqueous sodium hydroxide solution, and water was further added to make the total amount 100 parts.

Using the above-obtained ink for inkjet recording, inkjet recording described later in (B) was performed, and evaluation tests were conducted by the methods described later in (C) to (E). This is Example 5.

In addition, in the same manner as in Example 5 except that, in the following Table 2, the compound of the formula (8) obtained in Example 2 or the compound of the formula (9) obtained in Example 3 was respectively used instead of the compound of the formula (7) obtained in Example 1, an ink composition and an ink for inkjet recording was prepared. Using the obtained inks for inkjet recording, inkjet recording and evaluation tests were respectively conducted in the same manner as described above. The case where the compound of the formula (8) obtained in Example 2 was used is called Example 6, and the case where the compound of the formula (9) obtained in Example 3 was used is called Example 7.

TABLE 2

| | |
|---|---|
| Compound of Example 1 | 6.0 parts |
| Glycerine | 5.0 parts |
| Urea | 5.0 parts |
| N-methyl-2-pyrrolidone | 4.0 parts |
| IPA(isopropylalcohol) | 3.0 parts |
| Butyl carbitol | 2.0 parts |
| Surfactant (Surfynol$^{RTM}$ 104PG50 manufactured by Nissin Chemical Industry Co., Ltd.) | 0.1 part |
| 25% Aqueous NaOH + water | 74.9 parts |
| Total | 100.0 parts |

Comparative Examples 1 and 2

In the same manner as in Example 5 except that the compound No. 36 of Patent Literature 1 (compound of the following formula (11)) was used instead of the compound obtained in Example 1, an ink composition for comparison and an ink for inkjet recording were prepared, inkjet recording was performed using said ink, and the obtained recorded image was evaluated. This is Comparative Example 1.

In addition, in the same manner as in Example 5 except that the compound No. 32 of Example 1 in Patent Literature 10 (compound of the following formula (12)) was used instead of the compound obtained in Example 1, an ink composition and an ink for inkjet recording for comparison were prepared, inkjet recording was performed using said ink, and the obtained recorded image was evaluated. This is Comparative Example 2

The compound used in Comparative Example 1 is shown in the following formula (11) and the compound used in Comparative Example 2 is shown in the following formula (12), respectively.

Formula (11)

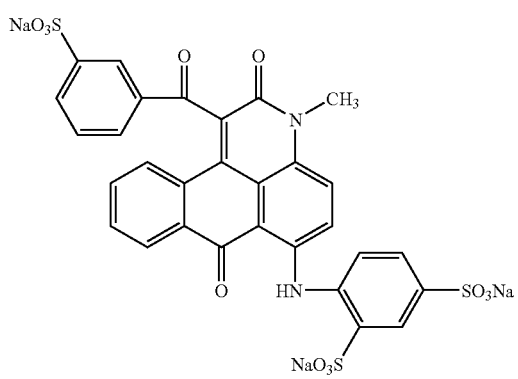

Formula (12)

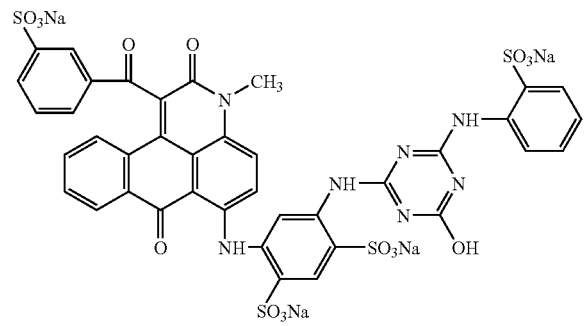

(B) Inkjet Recording

Using an inkjet printer (Canon Inc., trade name: Pixus® iP4100), inkjet recording was performed on three kinds of record-receiving materials which are inkjet professional papers having an ink receiving layer containing an porous white inorganic substance. These three kinds of inkjet professional papers (glossy papers) used in the evaluation tests are indicated below and called Glossy paper 1, Glossy paper 2 and Glossy paper 3, respectively. For inkjet recording, an image pattern was made so that print density could be obtained in several stages of gradation and a printed matter was made. Said printed matter was used as a test piece and the evaluation tests described in the following (C) to (E) were conducted, respectively.

Glossy paper 1: manufactured by Canon Inc., trade name: Professional Photopaper PR-101.
Glossy paper 2: manufactured by Seiko-Epson Corporation, trade name: CRISPIA®.
Glossy paper 3: manufactured by Hewlett Packard, trade name: Advanced Photo Paper.

(C) Hue Evaluation

Using a colorimetric system (GRETAG SPM50: manufactured by GRETAGMACBETH AG), the hue and vividness of recorded images of the printed test pieces were measured, and $L^*$, $a^*$ and $b^*$ values were calculated. Hue evaluation was conducted in comparison with a sample of Japan Color (JNC) Standard Magenta of JPMA (Japan Printing Machinery Manufacturers Association). In this regard, the part of each test piece having the same value of print density (D value) was used for measurement on each kind of glossy paper.

The results are shown in Table 3. The paper used for Japan Color Standard Magenta is Japan Color Standard Paper.

TABLE 3

| | Brightness | Chromaticity | |
| --- | --- | --- | --- |
| | $L^*$ | $a^*$ | $b^*$ |
| JNC Standard Magenta | 46.3 | 74.4 | −4.8 |
| Glossy paper 1 (D value = around 1.8) | | | |
| Example 5 | 47.1 | 84.0 | −5.8 |
| Example 6 | 50.0 | 82.2 | −2.9 |
| Example 7 | 46.9 | 81.7 | −11.7 |
| Comparative Example 1 | 40.5 | 84.3 | −22.9 |
| Comparative Example 2 | 39.8 | 84.0 | −26.1 |
| Glossy paper 2 (D value = around 2.0) | | | |
| Example 5 | 45.8 | 86.0 | −15.2 |
| Example 6 | 49.6 | 84.7 | −10.8 |
| Example 7 | 48.7 | 84.4 | −13.8 |
| Comparative Example 1 | 39.7 | 87.0 | −26.8 |
| Comparative Example 2 | 40.2 | 87.5 | −27.5 |
| Glossy paper 3 (D value = around 1.9) | | | |
| Example 5 | 48.0 | 84.1 | −6.6 |
| Example 6 | 51.3 | 82.8 | −3.5 |
| Example 7 | 47.2 | 84.1 | −18.1 |
| Comparative Example 1 | 41.3 | 87.1 | −25.6 |
| Comparative Example 2 | 41.5 | 87.8 | −27.3 |

As is clear from Table 3, it is found that chromaticities ($a^*$, $b^*$) of Examples 5 to 7 are approximate to that of the hue of JNC Standard Magenta with regard to any of Glossy papers 1 to 3. Particularly with regard to Glossy paper 1, Comparative Examples 1 and 2 have very low $b^*$ values of −22.9 and −26.1 while $b^*$ values of Examples 5 to 7 are −5.8, −2.9 and −11.7, which are extremely approximate to $b^*$ value (−4.8) of Standard Magenta, and thus it is found that the hues thereof are extremely close to that of Standard Magenta. In addition, there is also the same tendency with regard to Glossy papers 2 and 3. Further, Examples 5 to 7 have high brightness, having $L^*$ values higher than those of Comparative Examples 1 and 2 with regard to any of Glossy papers 1 to 3. From the above results, it is found that recorded images with an ink composition using the coloring matter of the present invention have such characteristics as having a hue which is very approximate to the hue of JNC Standard Magenta and has a high brightness.

Hereinafter, evaluation on fastnesses will be described. For fastnesses, two kinds of tests, ozone gas fastness and moisture fastness, were conducted and evaluated.

(D) Ozone Gas Fastness Test

Using an ozone weatherometer (manufactured by Suga Test Instruments Co., Ltd.), test pieces printed on Glossy papers 1 to 3 were left for 16 hours on the conditions of an ozone concentration of 40 ppm, a temperature of 24° C. and a humidity of 60% RH, and residual rate (%) of print density (D value=around 1.0) before and after irradiation were measured. Using a colorimetric system (GRETAG SPM50: manufactured by GRETAGMACBETH AG), with regard to residual rate of the test pieces, D value was measured before and after the tests of the print density (D value=around 1.0), and D value after the test/D value before the test was calculated as percentage. The results are shown in Table 4.

TABLE 4

|  | Glossy paper 1 | Glossy paper 2 | Glossy paper 3 |
| --- | --- | --- | --- |
| Example 5 | 76.3 | 86.8 | 80.9 |
| Example 6 | 75.2 | 81.9 | 77.5 |
| Example 7 | 75.7 | 84.7 | 85.0 |
| Comparative Example 1 | 55.0 | 50.4 | 54.5 |
| Comparative Example 2 | 62.1 | 65.2 | 69.5 |

As is clear from Table 4, Examples 5 to 7 have higher residual rates in comparison with Comparative Examples 1 and 2 with regard to all the Glossy papers. For example, with regard to Glossy paper 1, the residual rates of Comparative Examples 1 and 2 are 55.0 and 62.1 while the residual rates of Examples 5 to 7 are 76.3, 75.2, and 75.7 and thus higher.

With regard to Glossy paper 2, the residual rates of Comparative Examples 1 and 2 are 50.4 and 65.2 while the residual rates of Examples 5 to 7 are 86.8, 81.9 and 84.7 and thus very higher.

With regard to Glossy paper 3, the residual rates of Comparative Examples 1 and 2 are 54.5 and 69.5 while the residual rates of Examples 5 to 7 are 80.9, 77.5 and 85.0 and thus very higher.

Therefore, it is found that the ozone gas fastness of Examples 5 to 7 of the present invention is very good.

(E) Moisture Fastness Test

Using a thermo-hygrostat (manufactured by Ohken Co., Ltd.), test pieces printed on Glossy papers 1 were left for 96 hours on the conditions of a temperature of 50° C. and a humidity of 90% RH, bleeding was judgment before and after the test by visual observation and evaluated into 3 ranks. The results are shown in Table 6.

O: Bleeding is not observed.
Δ: Bleeding is slightly observed.
X: Bleeding is significantly observed.

TABLE 5

| Example 5 | O |
| --- | --- |
| Example 6 | O |
| Example 7 | O |
| Comparative Example 1 | X |
| Comparative Example 2 | O |

As is clear from Table 5, with regard to Glossy paper 1, bleeding of Comparative Example 1 is significantly observed while bleeding of any of Examples 5 to 7 is not observed, and thus it is found that the moisture fastness of Examples 5 to 7 is very good.

From the test results in Tables 3 to 5, it is clear that recorded images with an ink composition using the coloring matter of the present invention have such characteristics as having a hue which is very approximate to the hue of JNC Standard Magenta and has a very high brightness, and they are excellent in various fastnesses, particularly in ozone fastness and moisture fastness. Therefore, it can be said that the compound of the present invention is extremely excellent as a magenta coloring matter for ink for inkjet recording.

The invention claimed is:

1. An anthrapyridone compound represented by the following formula (1) or a salt thereof:

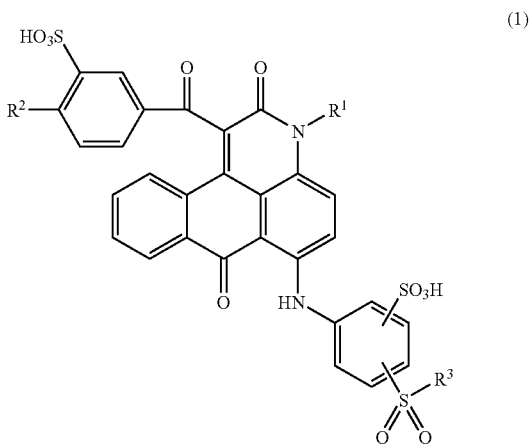

(1)

wherein,
R$^1$ represents a hydrogen atom, a lower alkyl group, a hydroxy lower alkyl group, a cyclohexyl group, a mono- or di-lower alkylamino lower alkyl group or a cyano lower alkyl group,
R$^2$ represents a hydrogen atom or a methoxy group,
R$^3$ represents an unsubstituted C5-C12 alkyl group; a substituted C5-C12 alkyl group having, as a substituent, a group selected from the group consisting of an aryl group, a heterocyclic group, a sulfonic acid group, a carboxy group, an alkoxycarbonyl group, an acyl group, a carbamoyl group, a cyano group, an alkoxy group, a phenylalkoxy group, a phenoxy group, a hydroxy group and a nitro group; an unsubstituted aryl group; a substituted aryl group having, as a substituent, a group selected from the group consisting of a halogen atom, a cyano group, a hydroxy group, a sulfonic acid group, a substituted or unsubstituted alkyl group, a carboxy group, an alkoxycarbonyl group, a carbamoyl group, an alkoxy group, a phenoxy group and a nitro group; an unsubstituted heteroaryl group; or a substituted heteroaryl group having, as a substituent, a group selected from the group consisting of a halogen atom, a cyano group, a hydroxy group, a sulfonic acid group, a substituted or unsubstituted alkyl group, a carboxy group, an alkoxycarbonyl group, a carbamoyl group, an alkoxy group, a phenoxy group and a nitro group; respectively, and with regard to the substitution positions of —SO$_2$R$^3$ and —SO$_3$H whose substitution position are not specified and the both of which the benzene ring has thereon, one of their substitution positions is the para-position and the other thereof is the ortho-position to the substitution position of the nitrogen atom by which said benzene ring is substituted.

2. The anthrapyridone compound or a salt thereof according to claim 1, wherein R$^1$ is a hydrogen atom or a methyl group.

3. The anthrapyridone compound or a salt thereof according to claim 1, wherein:
R$^1$ is a hydrogen atom or a methyl group, and
R$^3$ is an unsubstituted C6-C8 alkyl group; a substituted C6-C8 alkyl group having, as a substituent, a group selected from the group consisting of an aryl group, a heterocyclic group, a sulfonic acid group, a carboxy group, an alkoxycarbonyl group, an acyl group, a carbamoyl group, a cyano group, an alkoxy group, a phenoxy group, a hydroxy group and a nitro group; or a substituted phenyl group having, as a substituent, a sulfonic acid group or a carboxy group.

4. The anthrapyridone compound or a salt thereof according to claim 1, wherein:
$R^1$ is a methyl group, and $R^3$ is an unsubstituted C6 alkyl group; or a substituted phenyl group having a carboxy group as a substituent.

5. The anthrapyridone compound or a salt thereof according to claim 4, wherein $R^2$ is a hydrogen atom.

6. An ink composition comprising, as a coloring matter, the anthrapyridone compound or a salt thereof according to claim 1 or 4.

7. The ink composition according to claim 6, which further contains water and a water-soluble organic solvent.

8. The ink composition according to claim 7, which is for inkjet recording.

9. The ink composition according to claim 6, wherein the content of inorganic impurity contained in the total mass of the anthrapyridone compound represented by the following formula (1) or a salt thereof contained as a coloring matter is 1% by mass or less:

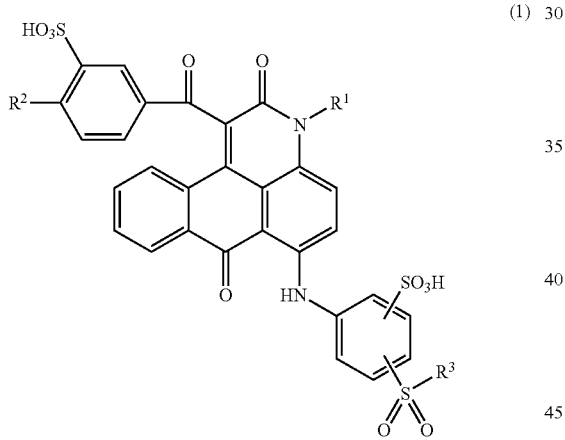

(1)

wherein, $R^1$ represents a hydrogen atom, a lower alkyl group, a hydroxy lower alkyl group, a cyclohexyl group, a mono- or di-lower alkylamino lower alkyl group or a cyano lower alkyl group, $R^2$ represents a hydrogen atom or a methoxy group, $R^3$ represents an unsubstituted C5-C12 alkyl group; a substituted C5-C12 alkyl group having, as a substituent, a group selected from the group consisting of an aryl group, a heterocyclic group, a sulfonic acid group, a carboxy group, an alkoxycarbonyl group, an acyl group, a carbamoyl group, a cyano group, an alkoxy group, a phenylalkoxy group, a phenoxy group, a hydroxy group and a nitro group; an unsubstituted aryl group; a substituted aryl group having, as a substituent, a group selected from the group consisting of a halogen atom, a cyano group, a hydroxy group, a sulfonic acid group, a substituted or unsubstituted alkyl group, a carboxy group, an alkoxycarbonyl group, a carbamoyl group, an alkoxy group, a phenoxy group and a nitro group; an unsubstituted heteroaryl group; or a substituted heteroaryl group having, as a substituent, a group selected from the group consisting of a halogen atom, a cyano group, a hydroxy group, a sulfonic acid group, a substituted or unsubstituted alkyl group, a carboxy group, an alkoxycarbonyl group, a carbamoyl group, an alkoxy group, a phenoxy group and a nitro group; respectively, and with regard to the substitution positions of —$SO_2R^3$ and —$SO_3H$ whose substitution position are not specified and the both of which the benzene ring has thereon, one of their substitution positions is the para-position and the other thereof is the ortho-position to the substitution position of the nitrogen atom by which said benzene ring is substituted.

10. The ink composition according to claim 6, wherein the content of the anthrapyridone compound represented by the following formula (1) or a salt thereof contained as a coloring matter is 0.1 to 20% by mass to the total mass of the ink composition:

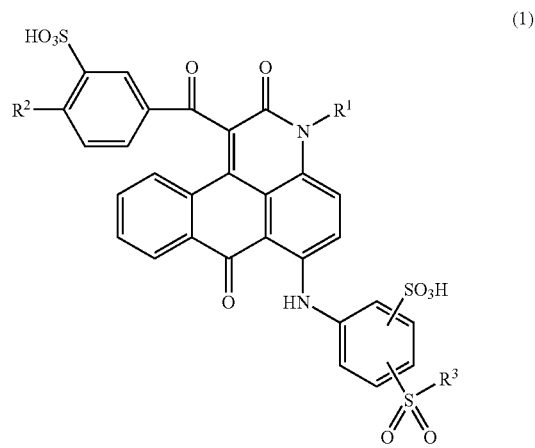

(1)

wherein, $R^1$ represents a hydrogen atom, a lower alkyl group, a hydroxy lower alkyl group, a cyclohexyl group, a mono- or di-lower alkylamino lower alkyl group or a cyano lower alkyl group, $R^2$ represents a hydrogen atom or a methoxy group, $R^3$ represents an unsubstituted C5-C12 alkyl group; a substituted C5-C12 alkyl group having, as a substituent, a group selected from the group consisting of an aryl group, a heterocyclic group, a sulfonic acid group, a carboxy group, an alkoxycarbonyl group, an acyl group, a carbamoyl group, a cyano group, an alkoxy group, a phenylalkoxy group, a phenoxy group, a hydroxy group and a nitro group; an unsubstituted aryl group; a substituted aryl group having, as a substituent, a group selected from the group consisting of a halogen atom, a cyano group, a hydroxy group, a sulfonic acid group, a substituted or unsubstituted alkyl group, a carboxy group, an alkoxycarbonyl group, a carbamoyl group, an alkoxy group, a phenoxy group and a nitro group; an unsubstituted heteroaryl group; or a substituted heteroaryl group having, as a substituent, a group selected from the group consisting of a halogen atom, a cyano group, a hydroxy group, a sulfonic acid group, a substituted or unsubstituted alkyl group, a carboxy group, an alkoxycarbonyl group, a carbamoyl group, an alkoxy group, a phenoxy group and a nitro group; respectively, and with regard to the substitution positions of —$SO_2R^3$ and —$SO_3H$ whose substitution position are not specified and the both of which the benzene ring has thereon, one of their substitution positions is the para-position and the other thereof is the ortho-position to the substitution position of the nitrogen atom by which said benzene ring is substituted.

11. A method for inkjet recording comprising discharging a droplet of an ink composition containing the anthrapyridone compound or a salt thereof according to claim 1 in response to a recording signal for recording on a record-receiving material.

12. The method for inkjet recording according to claim 11, wherein the record-receiving material is a communication sheet.

13. The method for inkjet recording according to claim 12, wherein the communication sheet is a communication sheet having an ink image-receiving layer containing a porous white inorganic substance.

14. A colored product colored with the ink composition according to claim 6.

15. The colored product according to claim 14, wherein coloring is performed by an inkjet printer.

16. An inkjet printer comprising a container containing the ink composition according to claim 6.

17. The anthrapyridone compound or a salt thereof according to claim 1, wherein $R^1$ is a methyl group, and $R^3$ is an unsubstituted C6-C8 alkyl group or a carboxy-substituted aryl group.

* * * * *